US00PP08756P

United States Patent [19]

VandenBerg

[11] Patent Number: Plant 8,756

[45] Date of Patent: May 31, 1994

[54] CHRYSANTHEMUM PLANT NAMED MEGAN

[75] Inventor: Cornelis P. VandenBerg, Salinas, Calif.

[73] Assignee: Yoder Brothers Inc., Barberton, Ohio

[21] Appl. No.: 822,700

[22] Filed: Jan. 21, 1992

[51] Int. Cl.[5] ..... A01H 5/00

[52] U.S. Cl. ..... Plt./74.1

[58] Field of Search ..... Plt. 74.1, 82.4, 76

*Primary Examiner*—Howard J. Locker

*Attorney, Agent, or Firm*—Foley & Lardner

[57] ABSTRACT

A Chrysanthemum plant named Megan particularly characterized by its flat capitulum form; decorative capitulum type with a high number of disc florets in the fall, to a daisy with 5 to 6 rows of ray florets in the spring; red-purple ray floret color; diameter across face of capitulum of 45 to 54 mm when fully opened; branching pattern is spreading and prolific, with 6 to 9 breaks after pinch when grown outside under natural daylength in fall flowerings and in 10 cm pots for spring flowerings; natural season flower date of August 23 to 29 when planting rooted cuttings on June 21 to 23 in Salinas, Calif., and of September 27 to October 5 when planting rooted cuttings June 15 to June 18 in Hightstown, N.J.; flowering response of 48 to 49 days after rooting in no light/no shade programs in spring in Salinas; plant height of 30 to 36 cm when grown in fall under natural daylength with no growth regulators in New Jersey, and of 15 to 25 cm when grown in 10 cm pots in spring with 1 application of 2500 ppm B-9 SP; and durable, uniform performance.

4 Drawing Sheets

The present invention comprises a new and distinct cultivar of Chrysanthemum, botanically known as *Dendranthema grandiflora,* and referred to by the cultivar name Megan.

Megan, identified as 8315 (85-125002), was originated from a cross made by Cornelis P. VandenBerg in a controlled breeding program in Salinas, Calif., in 1985.

The female parent of Megan was an unnamed seedling identified as 2941 (82-N14003) and described as a spray pot mum and garden mum with a flat capitulum form; a decorative capitulum type; a lavender-pink ray floret color, a diameter across face of capitulum of 57 to 64 mm when fully opened; an average plant height of 28 to 37 cm from soil line at time of flowering based on June 14 planting in Hightstown, N.J.; a spreading and prolific branching pattern, averaging 7–9 branches per plant after pinch; an average natural season flower date of August 20 to August 29 in Salinas, Calif., and of September 28 to October 1 in Hightstown, N.J.; and a photoperiodic flowering response to short days of 45 to 49 days in spring flowering programs.

The male parent of Megan was an unnamed seedling identified as 0292 (83-631002) and described as a spray pot mum and garden mum with a flat capitulum form; a daisy capitulum type; a bronze ray floret color; a plant height of 28 to 33 cm from soil line at time of flowering based on June 14 to 16 planting in Hightstown, N.J.; a spreading and prolific branching pattern, averaging 8 to 9 branches per plant after pinch; a natural season flower date of August 28 to 30 in Salinas, Calif., and of September 26 to 30 in Hightstown, N.J.; and a photoperiodic flowering response to short days of 46 to 52 days in photoperiodic controlled flowering programs.

Megan was discovered and selected as one flowering plant within the progeny of the stated cross by Cornelis P. VandenBerg on Jan. 16, 1986, in a controlled environment in Salinas, Calif.

The first act of asexual reproduction of Megan was accomplished when vegetative cuttings were taken from the initial selection in Mar. 1986 in a controlled environment in Salinas, Calif., by technicians working under supervision of Cornelis P. VandenBerg.

Horticultural examination of controlled flowerings of successive plantings has shown that the unique combination of characteristics as herein disclosed for Megan are firmly fixed and are retained through successive generations of asexual reproduction.

Megan has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif. and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Megan, which, in combination, distinguish this Chrysanthemum as a new and distinct cultivar:

1. Flat capitulum form.
2. Decorative capitulum type with a relatively high number of disc florets in the fall compared to typical decorative type cultivars, to a daisy with 5 to 6 rows of ray florets in the spring.
3. Red-purple ray floret color.
4. Diameter across face of capitulum of 45 to 54 mm when fully opened.
5. Branching pattern is spreading and prolific, with 6 to 9 breaks after pinch when grown outside under natural daylength in fall flowerings and in 10 cm pots for spring flowerings.
6. Natural season flower date of August 23 to 29 when planting rooted cuttings on June 21 to 23 in Salinas, Calif., and of September 27 to October 5 when planting rooted cuttings June 15 to June 18 in Hightstown, N.J.

7. Flowering response of 48 to 49 days after rooting in no light/no shade programs in spring in Salinas.

8. Plant height of 30 to 36 cm when grown in fall under natural daylength with no growth regulators in New Jersey, and of 15 to 25 cm when grown in 10 cm pots in spring with 1 application of 2500 ppm B-9 SP.

9. Plants within the same plot flower uniformly, and the flowers are long lasting.

The accompanying photographic drawings show typical inflorescence and leaf characteristics of Megan, with the colors being as nearly true as possible with illustrations of this type. Sheet 1 is a color photograph of Megan grown as a pinched spray pot mum with 1 cutting in a 10 cm pot. Sheet 2 is a black and white photograph of three views of the inflorescence of Megan. Sheet 3 is a black and white photograph showing the upper and under sides of the leaves of Megan at 3 stages of development (mature, intermediate and immature). In sheets 2 and 3 a measuring tape in centimeters has been added. Sheet 4 is a color photograph taken in late September of a plant of Megan grown under natural season flower conditions in Hightstown, N.J. with the photo clearly showing the decorative type. The ray floret color depicted in this photo is a much redder-purple than the true ray floret color, which is precisely shown in the color photo comprising Sheet 1.

Of the commercial cultivars known to the inventor, the most similar in comparison to Megan is the cultivar identified as Stardom, disclosed in U.S. Plant Pat. No. 3,530. Reference is made to attached Chart A, which compares certain characteristics of Megan to the same characteristics of Stardom.

Similar traits are capitulum form and type and branching pattern. When compared with Stardom, Megan has a darker ray floret color, significiantly smaller diameter of capitulum, a slightly faster fall natural season flowering response in California, but a slower flowering response in New Jersey, and a taller plant height in natural season flowerings.

In the following description color references are made to The Royal Horticultural Society Colour Chart. The color values were determined on plant material grown as a pinched spray pot mum in a 10 cm pot in Salinas, Calif. on Apr. 17, 1991.

Classification:

*Botanical.*—*Dendranthema grandiflora* cv Megan.

*Commercial.*—Flat decorative to daisy spray pot mum and garden mum.

I. INFLORESCENCE

A. Capitulum:

*Form.*—Flat.

*Type.*—Decorative with many disc florets in natural season fall flowering, to daisy with 5 to 6 rows of ray florets in spring flowerings.

*Diameter across face.*—45 to 54 mm. when fully opened.

B. Corolla of ray florets:

*Color (general tonality from a distance of three meters).*—Red-purple.

*Color (upper surface).*—70B to 70C.

*Color (under surface).*—70B to 70C.

*Shape.*—See photograph.

C. Corolla of disc florets:

*Color (mature).*—14B.

*Color (immature).*—144B.

D. Reproductive organs:

*Androecium.*—Present on disc florets only; moderate pollen.

*Gynoecium.*—Present on both ray and disc florets.

PLANT

A. General appearance:

*Height.*—30 to 36 cm when grown in fall under natural day-length in California and in New Jersey with no growth regulators, and of 15 to 25 cm when grown in 10 cm pots in spring in Salinas with 1 application of 2500 ppm B-9 SP.

*Branching pattern.*—Spreading and prolific, with 6 to 9 breaks after pinch when grown outside under natural daylength in fall flowerings and in 10 cm pots for spring flowerings.

B. Foliage:

*Color (upper surface).*—147A.

*color (under surface).*—147B.

*Shape.*—See photograph.

CHART A

| Characteristic | Megan | STARDOM |
|---|---|---|
| Ray floret color | Red-purple | Light lavender |
| Capitulum form and type | Flat; daisy to decorative | Flat; daisy to decorative |
| Diameter across face of capitulum | 45 to 54 mm | 64 to 70 mm |
| Branching pattern | Spreading and prolific | Spreading and prolific |
| Nat. season flower data: | | |
| in Salinas, CA | Aug 23 to 29 | Aug 30 to 31 |
| in Hightstown, NJ | Sep 27 to Oct 5 | Sep 25 to 30 |
| Controlled response | 48 to 49 days | 45 to 52 days |
| Plant height: | | |
| in natural season fall | 30 to 36 cm | 25 to 33 cm |
| in 10 cm pots spring | 15 to 25 cm | 20 to 23 cm |

COMPARISONS MADE OF PLANTS GROWN AS UNDER NATURAL SEASON OUTDOOR CONDITIONS IN SALINAS, CALIFORNIA AND IN HIGHTSTOWN, NEW JERSEY AND IN SPRING FLOWERING PROGRAMS IN SALINAS, CALIFORNIA

I claim:

1. A new and distinct Chrysanthemum plant named Megan, as described and illustrated.

* * * * *

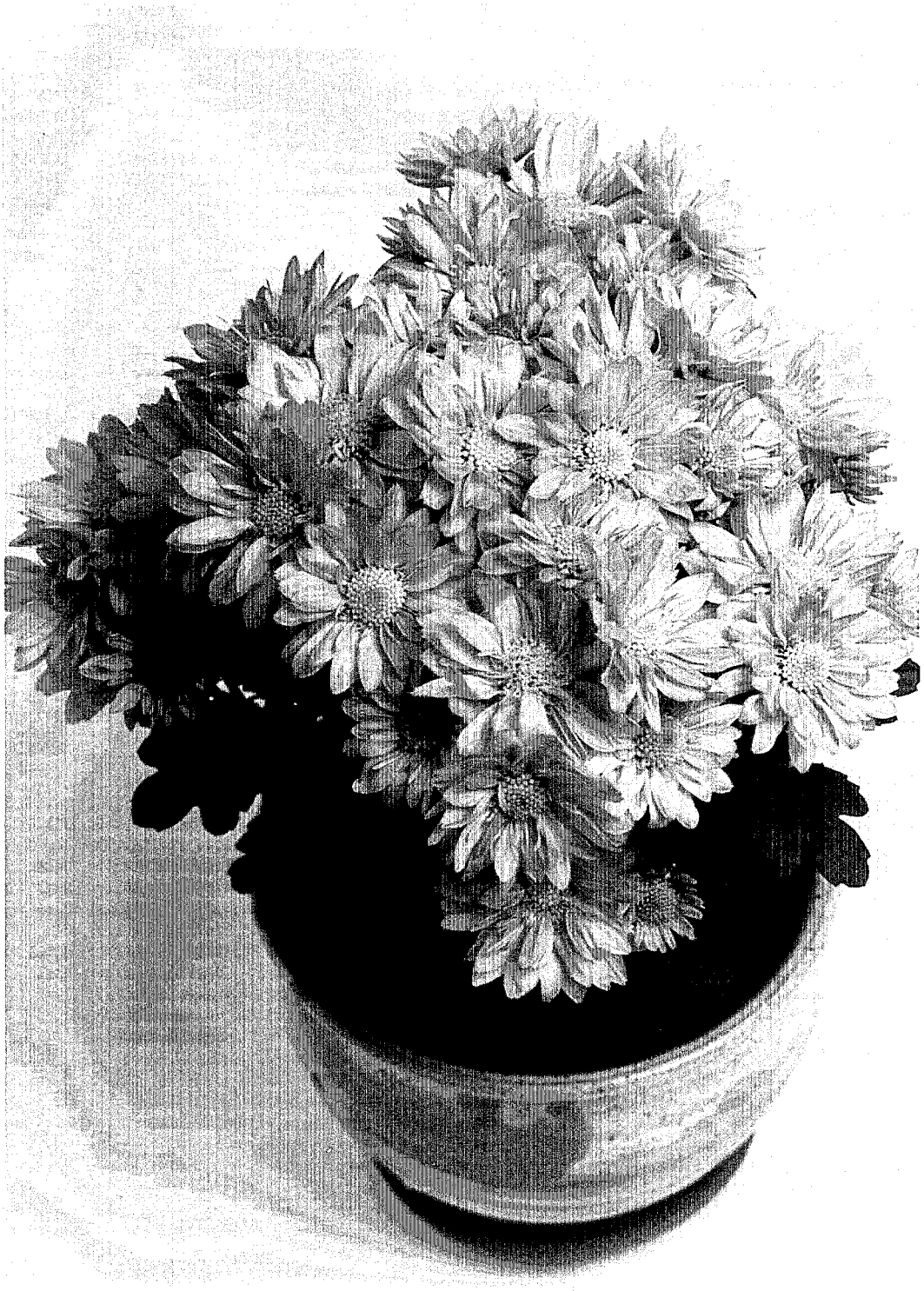

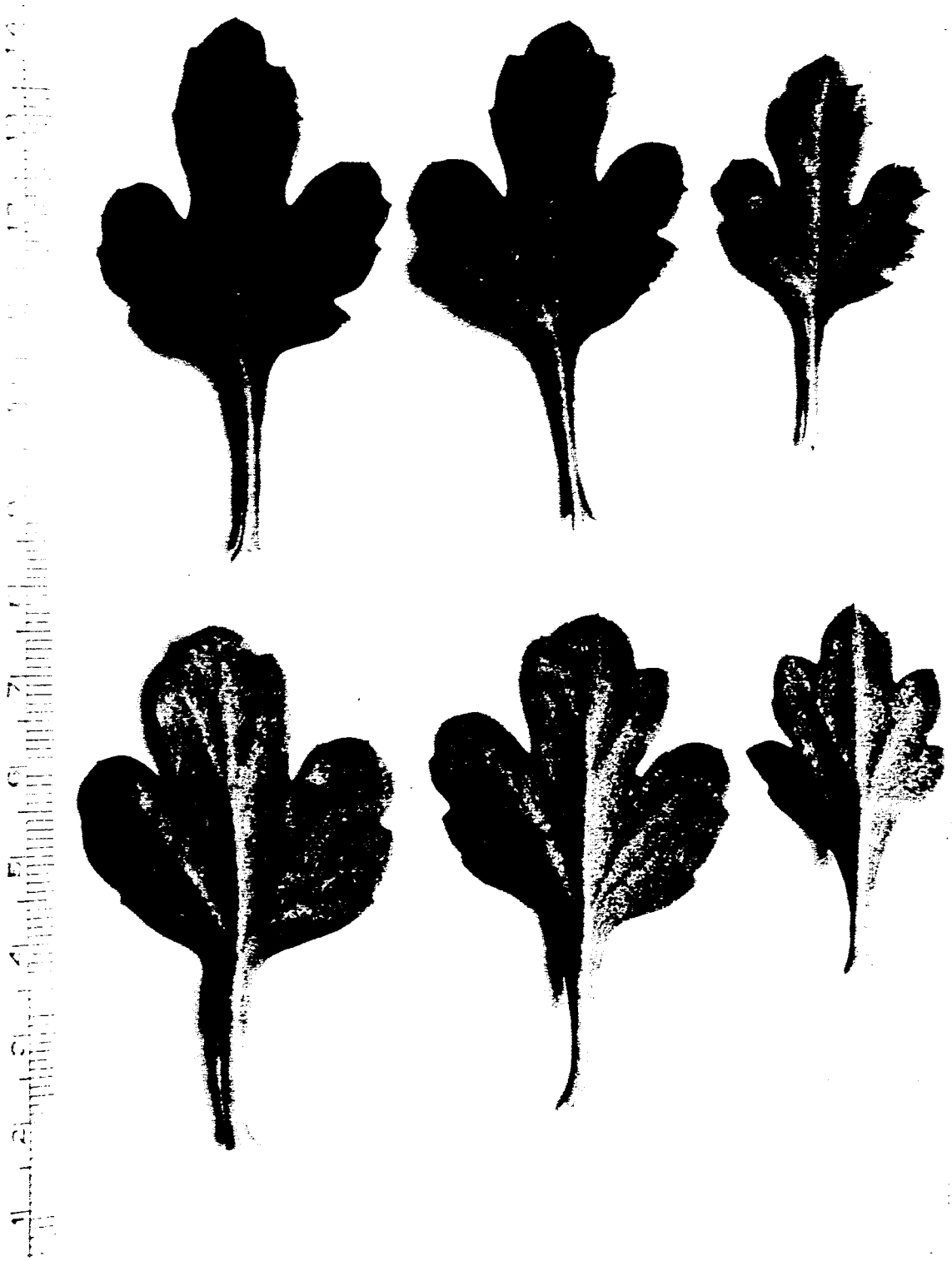

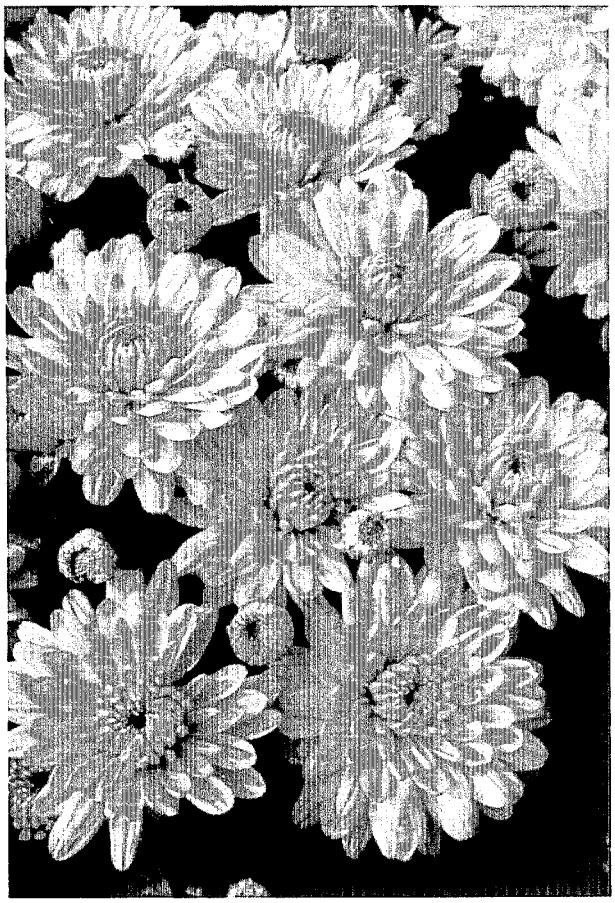

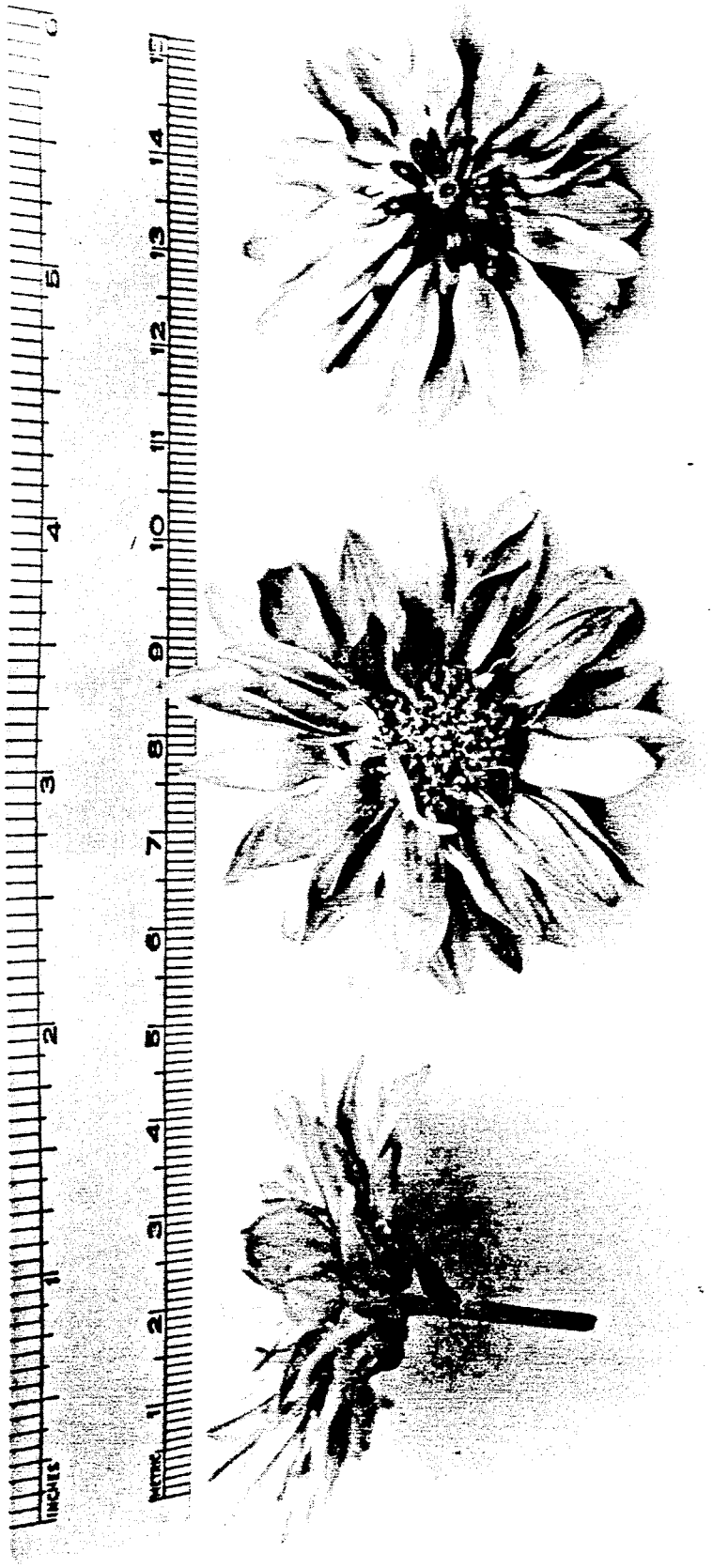
INCHES
METRIC